(12) United States Patent
Hill et al.

(10) Patent No.: US 6,442,429 B1
(45) Date of Patent: Aug. 27, 2002

(54) METHOD AND APPARATUS FOR DIAGNOSIS AND TREATMENT OF ARRHYTHMIAS

(75) Inventors: Michael R. S. Hill; Michael F. Hess, both of Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 39 days.

(21) Appl. No.: 09/593,200

(22) Filed: Jun. 14, 2000

Related U.S. Application Data
(60) Provisional application No. 60/139,962, filed on Jun. 18, 1999.

(51) Int. Cl.⁷ .................................................. A61N 1/362
(52) U.S. Cl. ........................................................ 607/14
(58) Field of Search ................................ 607/4, 5, 14, 9

(56) References Cited

U.S. PATENT DOCUMENTS

| | | | |
|---|---|---|---|
| 4,316,472 A | 2/1982 | Mirowski et al. | 128/419 D |
| 4,375,817 A | 3/1983 | Engle et al. | 128/419 D |
| 4,384,585 A | 5/1983 | Zipes | 128/419 D |
| 4,577,633 A | 3/1986 | Berkovits et al. | 128/419 PG |
| 4,587,970 A | 5/1986 | Holley et al. | 128/419 PG |
| 4,726,380 A | 2/1988 | Vollmann et al. | 128/419 PG |
| 4,727,877 A | 3/1988 | Kallok | 128/419 D |
| 4,800,883 A | 1/1989 | Winstrom | 128/419 D |
| 4,830,006 A | 5/1989 | Haluska et al. | 128/419 PG |
| 4,880,005 A | 11/1989 | Pless et al. | 128/419 PG |
| 4,941,471 A | 7/1990 | Mehra | 128/419 PG |
| 4,949,719 A | 8/1990 | Pless et al. | 128/419 D |
| 4,953,551 A | 9/1990 | Mehra et al. | 128/419 D |
| 5,052,388 A | 10/1991 | Sivula et al. | 128/419 PG |
| 5,086,772 A | 2/1992 | Larnard et al. | 128/419 D |
| 5,088,488 A | 2/1992 | Markowitz et al. | 128/419 PG |
| 5,107,850 A | 4/1992 | Olive | 128/705 |
| 5,117,824 A | 6/1992 | Keimel et al. | 128/419 D |
| 5,161,527 A | 11/1992 | Nappholz et al. | 128/419 PG |
| 5,163,427 A | 11/1992 | Keimel | 128/419 D |
| 5,188,105 A | 2/1993 | Keimel | 128/419 D |
| 5,217,021 A | 6/1993 | Steinhaus et al. | 128/702 |
| 5,269,301 A | 12/1993 | Cohen | 607/6 |
| 5,522,859 A | 6/1996 | Stroebel et al. | 607/19 |
| 5,545,185 A | 8/1996 | Denker | 607/14 |
| 5,713,929 A | 2/1998 | Hess et al. | 605/14 |
| 5,846,263 A | 12/1998 | Peterson et al. | 607/14 |
| 5,855,593 A | 1/1999 | Olson et al. | 607/9 |
| 6,058,328 A * | 5/2000 | Levine et al. | 607/14 |

FOREIGN PATENT DOCUMENTS

| | | | |
|---|---|---|---|
| EP | 0624386 | 11/1994 | |
| WO | 9218198 | 10/1992 | A61N/1/39 |
| WO | 9416768 | 8/1994 | |
| WO | 9528987 | 11/1995 | A61N/1/39 |
| WO | 9528988 | 11/1995 | A61N/1/39 |
| WO | 9825670 | 6/1998 | |
| WO | 9832489 | 7/1998 | |

* cited by examiner

*Primary Examiner*—Scott Getzow
(74) *Attorney, Agent, or Firm*—Girma Wolde-Michael

(57) ABSTRACT

A medical device selects the most appropriate among various calculated escape intervals for use in the next cardiac cycle. This is particularly implemented in cardiac event in which a pacemaker is used to prevent multiple tachyarrhythmias. The prevention pacing modes may be simultaneously active, with the escape interval for each mode calculated and updated on a beat-by-beat basis. The medical device selects tachyarrhythmia prevention pacing modality to control the escape interval of the current cardiac cycle in order that a more appropriate method for calculating the escape interval based on the present condition of the patient, may be selected.

8 Claims, 10 Drawing Sheets

METHOD AND APPARATUS FOR DIAGNOSIS AND TREATMENT OF ARRHYTHMIAS

This application claims the benefit of provisional application 60/139,962 filed on Jun. 18, 1999.

BACKGROUND OF THE INVENTION

This invention relates to devices which detect and/or treat tachyarrhythmias (rapid heart rhythms), and more specifically, to the operation of arrhythmia prevention pacing modes which vary the pacing rate on a beat by beat basis in such devices.

In addition to delivery of pacing pulses to terminate tachyarrhythmias and to treat bradycardias, a number of pacing modes have been recently developed which are intended to prevent the occurrence of tachyarrhythmias. These pacing modalities can generally be described as "tachyarrhythmia prevention pacing modes", and include, for example, ventricular rate stabilization pacing as disclosed in U.S. Pat. No. 4,941,471 issued to Mehra, an improved version of ventricular rate stabilization pacing as disclosed in U.S. Pat. No. 5,545,185, issued to Denker et al, atrial rate stabilization pacing as disclosed in U.S. Pat. No. 5,846,263 issued to Peterson et al, and an atrial pacing preference modality as disclosed in U.S. Pat. No. 5,522,859 issued to Hess et al., all of which are incorporated herein by reference in their entireties.

The tachyarrhythmia prevention pacing modalities described in the above patents attempt to prevent the occurrence of tachyarrhythmias by varying the interval between pacing pulses in a chamber of the heart, either the atrium or the ventricle, on a beat by beat basis. When incorporated in implantable devices, these pacing prevention modes are typically activated singly, as the proposed beat to beat change in pacing rate may differ substantially from one pacing modality to another. While it has been proposed to provide a pacemaker which automatically selects which of a number of available tachyarrhythmia prevention pacing modes is employed, as described in U.S. patent application Ser. No. 09/135,331, filed Aug. 17, 1998 by Mehra et al, and incorporated herein by reference in its entirety, the prior art typically envisions that only a single tachyarrhythmia prevention pacing mode will be operative at any one time.

SUMMARY OF THE INVENTION

The present invention is directed toward providing a pacemaker in which multiple tachyarrhythmia prevention pacing modes may be simultaneously active, with the escape intervals for each mode being calculated and updated on a beat by beat basis, with the device selecting the most appropriate of the various calculated escape intervals for use during the next cardiac cycle. The device makes the decision as to which tachyarrhythmia prevention pacing modality is employed to control the escape interval of the current cardiac cycle in order that the more appropriate method for calculating the escape interval, based on the present condition of the patient, may be selected.

A variety of criteria may be employed in order to select between the escape intervals provided by the tachyarrhythmia prevention pacing modes concurrently in operation. For example, one simple implementation would be to simply select the shorter of the calculated escape intervals. An alternative mechanism might be to employ the escape interval which represents the smallest net beat to beat change of escape interval. Yet an additional alternative would be to employ the calculated pacing rate of one of the pacing modalities preferentially, unless it differs by greater than a predetermined amount or percentage from the escape interval calculated by the second pacing modality, in which case the escape interval calculated by the second pacing modality would be employed. An additional alternative mechanism for selecting between the escape intervals provided by the two facing modalities would be to employ a criterion based decision methodology, in which selection of pacing escape interval is determined as a function of the operational history of the device, looking to previous frequencies of occurrences of arrhythmias associated with the various pacing modalities in situations similar to that associated with the present escape interval. In the context of the present invention, it is envisioned that the available arrhythmia prevention pacing modalities, in preferred embodiments, may be automatically disabled in response to detection or pre-detection of tachyarrhythmias in the atria and/or ventricles of the heart. The criteria employed for disabling the arrhythmia prevention pacing modalities may be the same for each pacing modality or may differ.

One of the tachyarrhythmia prevention pacing modes provided by the present invention may be an Atrial Rate Stabilization pacing mode, as described in U.S. Pat. No. 5,843,263, issued to Peterson et al, incorporated herein by reference in its entirety. The Atrial Rate Stabilization (ARS) pacing mode is similar in some respects to that disclosed in U.S. Pat. No. 5,713,929, issued to Mehra et al, but particularly adapted to controlling atrial pacing rate. In this pacing modality, the pacemaker-defined escape interval following a paced or sensed beat is set equal to the interval separating the paced or sensed beat from the preceding paced or sensed beat (preceding heart cycle length), plus an increment. The increment may be either a fixed value or more preferably a value which varies as a function of the preceding cycle length. This pacing modality eliminates the pauses following premature atrial beats and gradually returns the atrial cycle to its programmed or otherwise determined base value.

A second tachyarrhythmia prevention pacing mode provided by the present invention may be an Atrial Pacing Preference mode (APP), as described in U.S. Pat. No. 5,522,859 issued to Hess et al., incorporated herein by reference in its entirety. This pacing modality is adapted to deliver atrial pacing pulses at just above the sinus rate, in order to eliminate or reduce the frequency of atrial tachycardia and atrial fibrillation. In general, the sinus rate is a rate determined by periodically or at predetermined times reducing the pacing rate until a natural rhythm of heart beats is found in the atrium, (i.e., sinus node generated atrial depolarizations) and then increasing the paced rate again by a predetermined amount. When enabled, this pacing modality operates by initially decreasing the atrial escape interval on consecutive beats until atrial pacing is established. After a programmable number of beats, the escape interval is be increased incrementally until intrinsic atrial activity is once again discovered. When atrial intrinsic depolarizations are sensed, then the escape interval is decreased in increments until consistent atrial pacing is restored.

DETAILED DESCRIPTION OF THE PREFERRED EMBODIMENTS

Figure 1:
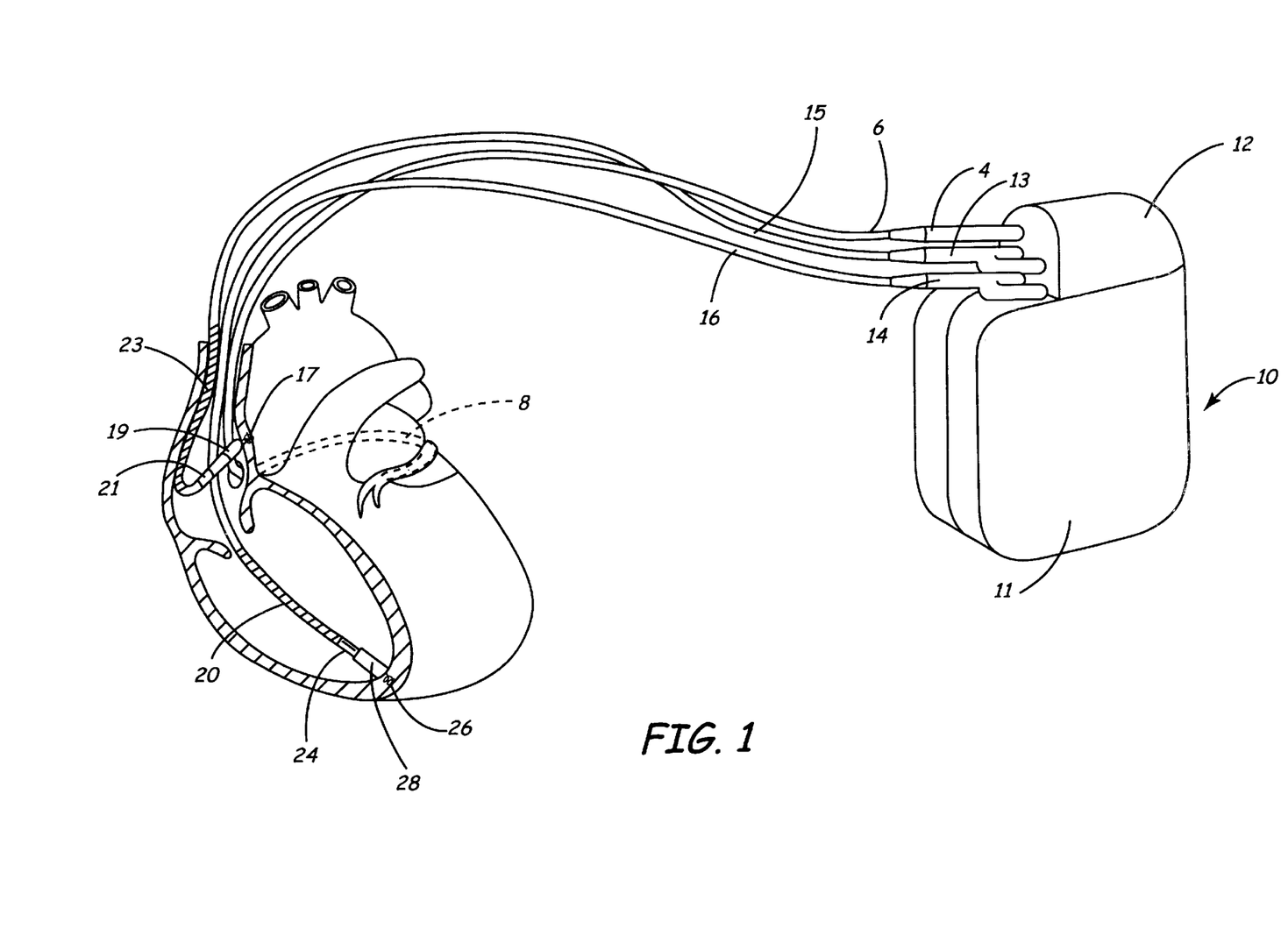
FIG. 1 illustrates a first embodiment of an implantable pacemaker/cardioverter/defibrillator of a type appropriate for use in practicing the present invention, in conjunction with a human heart.

FIG. 1 illustrates a defibrillator and lead set of a type appropriate for use in practicing the present invention. It should also be understood that the invention may also be practiced in a pacemaker which does not include cardioversion or defibrillation capabilities. The ventricular lead includes an elongated insulative lead body 16, carrying three mutually insulated conductors. Located adjacent the distal end of the lead are a ring electrode 24, an extendible helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three conductors, corresponding generally to the structure of the ventricular lead. Located adjacent the J-shaped distal end of the lead are a ring electrode 21 and an extendible helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. Electrode 23 preferably configured to extend from the SVC toward the tricuspid valve. At the proximal end of the lead is a bifurcated connector 13 which carries three electrical connectors, each coupled to one of the conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the conductor.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may op course be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
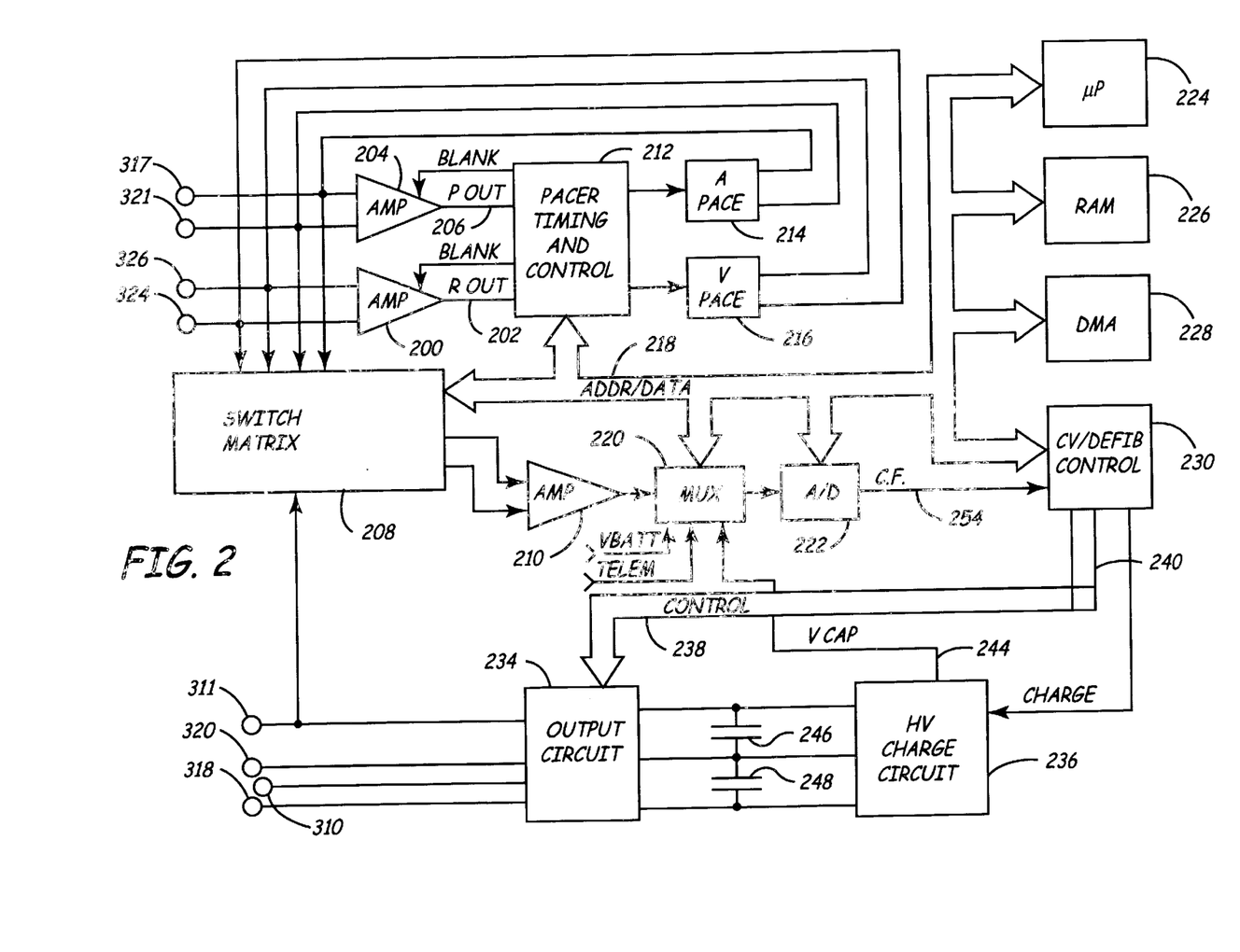
FIG. 2 illustrates a functional schematic diagram of an implantable pacemaker/cardioverter/defibrillator in which the invention may be practiced.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias and/or ventricular arrhythmias, cardioverters and defibrillators which do not provide antitachycardia pacing therapies, antitachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204. which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be per-formed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 (FIG. 4) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include prior art tachyarrhythmia detection algorithms. As described below, the arrhythmia detection and classification method according to the disclosed preferred embodiment of the invention corresponds to that presently employed in the Medtronic Gem™ implantable pacemaker cardioverter defibrillators. The arrhythmia detection and classification system in such embodiment employs a prioritized set of inter-related rules for arrhythmia detection, as described in U.S. Pat. No. 5,855,593, issued to Olson et al. or U.S. Pat. No. 5,755,736, issued to Gillberg et al., both incorporated herein by reference in their entireties. However, any of the various arrhythmia detection methodologies known to the art might also usefully be employed in alternative embodiments of the invention, including those described in U.S. Pat. No. 4,830,006, issued to Pless et al, U.S. Pat. No. 4,217,021, issued to Steinhaus, U.S. Pat. No. 5,086,772, issued to Lanard et al., U.S. Pat. No. 5,161,527, issued to Nappholz et al., U.S. Pat. No. 5,107,850, issued to Olive, U.S. Pat. No. 5,330,505, issued to Cohen or U.S. Pat. No. 5,269,301, issued to Cohen, all incorporated herein by reference in their entireties.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties. In addition, high frequency pulse bursts may be delivered to electrodes 317 and 321 to terminate atrial tachyarrhythmias, as described in PCT Patent Publication No. WO95/28987, filed by Duffin et al and PCT Patent Publication No. WO95/28988, filed by Mehra et al, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modem implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, high frequency burst stimulation as discussed above may be employed as the initial attempted therapy. Subsequent therapies may be delivery of high amplitude defibrillation pulses, typically in excess of 5 joules. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

In the context of the present invention, multiple tachyarrhythmia prevention pacing modes are provided, which are operative simultaneously to calculate escape intervals preceding the next delivered pacing pulse. For purposes of understanding the operation of the device, a description of each of two tachyarrhythmia prevention pacing modes follows. A description of the methods by which the device may select between the escape intervals calculated according to the two pacing modalities follows thereafter.

ARS and APP pacing is provided by the device in the same fashion as other pacing modalities, with the timing of escape intervals and refractory periods and the measurement of intervals between sensed and paced events accomplished by pacer timing and control circuitry 212, as described above. Microprocessor 224 performs the required calculations as described below, based on stored programming in its associated ROM and controls operation of the timers and associated logic in pacer timing and control circuitry 212. The various programmed and derived values described below are stored in RAM 226. In the embodiment of the invention disclosed herein, ARS and APP pacing modes are available when the permanent pacing mode is AAI, AAIR, DDD or DDDR.

The following terms should be understood in conjunction with the discussion of ARS and APP pacing modes which follows:

Lower Rate Interval (LRI)—The interval corresponding to the programmed base pacing rate. This value may be programmed, for example corresponding to 40–120 beats per minute. In the context of rate responsive pacing modes, e.g. DDDR, AAIR, it may serve as the lowest available pacing rate.

ARS Interval Increment (AARS)—The increment added to the previous atrial cycle length to define the atrial escape interval in ARS pacing. The increment may be either a programmed fixed value or more preferably a value which varies as a function of the preceding atrial cycle length. For example, AARS may be set to be 12–50% of the previous A-A interval, typically 25%.

Sense AV delay (SAV)—The programmed AV escape interval following a sensed atrial depolarization.

Paced AV delay (PAV)—The programmed AV escape interval following an atrial pacing pulse. Applicable to DDD, DDDR pacing. Typical values range from 100—250 ms. In a rate responsive device, the duration of the SAV and PAV may decrease with increasing pacing rates, as in some currently marketed pacemakers. Although not disclosed herein, in some embodiments of the invention the SAV and PAV intervals may also decrease with increasing sensed atrial rates, also as in some currently marketed pacemakers.

Ventricular upper rate interval (UTRI)—The minimum interval separating ventricular pacing pulses. Typically 400–600 ms.

Preceding A-A interval (AAlast)—The interval separating an atrial event, paced or sensed, from the immediately preceding atrial event, paced or sensed. Applicable to AAI, AAIR, DDD and DDDR pacing modes.

Atrial refractory period (ARP)—The atrial refractory period following an atrial event. Applicable to AAI pacing. Typically 250–400 ms.

Post-ventricular atrial refractory period (PVARP)—The atrial refractory period following a ventricular event. Applicable to DDD, DDDR pacing. Typically 250–400 ms.

PVC Post-ventricular atrial refractory period (PVARPpvc)—The atrial refractory period following a ventricular event sensed outside of the SAV or PAV intervals, if the feature is activated. Applicable to DDD, DDDR pacing. Typically about 400 ms and preferably greater than PVARP, and less than LRI-—PAV −300 ms.

Total atrial refractory period (TARP) The sum of SAV or PAV and PVARP in DDD mode.

Minimum ARS interval (ARSImin)—The programmed minimum duration of ARSI. Applies to AAI, AAIR, DDD and DDDR modes. Ranging from 300–700 ms. Typically about 500–600 ms.

Upper sensor rate interval (USRI)—the escape interval equal to the maximum sensor indicated pacing rate. This value may be set equal to UTRI.

Current escape interval (CEI)—the escape interval determined by the sensor in DDDR and AAIR pacing modes, or the programmed lower rate interval (LRI) in AAI or DDD modes.

Atrial pacing preference interval (APPI)—the calculated escape interval for use in atrial preference pacing (APP).

Minimum APP interval (APPImin)—the programmed minimum duration of APPI, set equal to ARSImin.

APP decrement (APPID)—the stepwise decrement employed by the atrial pacing preference modality during times in which the pacing rate is increased. May range, for example, from 30–150 milliseconds, typically approximately 50 milliseconds.

Atrial pacing preference interval increment (APPII)—the beat by beat increment in escape intervals employed by the atrial pacing preference (APP) mode during decreases in pacing rates. May be, for example, 10 to 150 milliseconds, typically about 20 milliseconds. Must be less than APPID.

Atrial pacing preference delay beats (APP Delay Beats)—the number of successive atrial paces required in order to initiate decreases in the APP defined pacing rate.

1. ARS Pacing

ARS pacing is intended to prevent occurrences of compensatory pauses in following premature beats, as described in the above-cited Mehra '929 patent, but in the particular embodiment disclosed herein, timed based upon atrial events. On each non-refractory atrial event the atrial escape interval is set to the ARS interval (ARSI) which is computed from the measured previous A-A interval (AAlast), the programmed ARS Interval Increment (AARS), the current escape interval (CEI) and the programmed Minimum ARS interval (ARSImin). ARSI interval is bounded to be greater than or equal to the ARSImin and less than or equal to CEI, according to the following equation. ARSI=Min{Max (ARSImin, AAlast+AARS) CEI}. In other words, ARSI is set equal to the value of the previous A-A interval, paced or sensed, plus the programmed increment, so long as the sum is less than CEI and greater than ARSImin, and is otherwise set equal to CEI or ARSImin. In the event that CEI is less than ARSImin, ARSI is set to CEI, so that the sensor indicated rates in DDDR and AAIR modes takes precedence over the otherwise calculated value of ARSI. If AAlast is unknown, for example following therapy or following the ARS pacing mode either being programmed ON, the ARSI will be LRI.

In DDD and DDDR modes, only in response to atrial events sensed during an atrial refractory period and outside of the defined minimum R-P interval from a preceding paced or sensed ventricular event within the SAV or PAV interval, the ARSI atrial escape interval in effect is canceled and the atrial escape interval (as timed from the preceding non-refractory sensed atrial depolarization or atrial pacing pulse) is reset according to the following equation. ARSI=Min (Max((2*AAlast+AARS),(AAlast+ARSImin)) ARSIlast). Otherwise, the ARSI in effect is unaltered. Once an ARSI has been canceled by a refractory atrial sensed event, subsequent refractory sensed atrial events have no effect on the atrial escape interval underway. Refractory sensed events and A-A intervals therebetween are, however, used to determine the value of the most recent A-A interval, for purposes of calculating the next ARSI.

Since a refractory sensed atrial event will not initiate timing of an ARSI initiated on the sensed event, the 'effective' Minimum ARS Interval is the atrial refractory period (ARP) plus AARS in AAI or AAIR mode and the total atrial refractory period (TARP) Plus AARS in DDD or DDDR mode. TARP in DDD or DDDR mode is typically about 450 ms. In some patients, this may be too long for ARS to be effective. In these cases a shorter PVARP will have to be programmed if ARS pacing is desired. The ARP and TARP define minimum coupling intervals for sensed atrial events to which ARS pacing is applied. ARSImin limits the resulting atrial pacing escape interval. As such, a long programmed TARP or ARP could functionally over-ride a short programmed ARSImin, and users should therefore program these two parameters in a coordinated fashion. The microprocessor prevents programming of ARSImin to be less than VTDI, as defined above, if VT Detection is ON, or less than VFDI, as defined above, if VF Detection is ON. These interlocks guard against atrial pacing cross talk to the ventricular sense amplifier resulting in inappropriate detection of VT or VF.

Ventricular events sensed within the programmed, PAV and SAV intervals, including ventricular pacing pulses delivered at the ends of the PAV and SAV intervals have no affect on timing of the ARSI underway. The effect of a ventricular sensed event, such as a PVC, outside the PAV or SAV interval in DDD or DDDR mode is to initiate a new atrial escape interval or V-A interval, calculated according to the following equation. V-A=Min(CEI, ARSI)–PAVcurrent). If the SAV interval is extended to the expiration of UTRI, as occurs during "pseudo-Wenckebach" upper rate behavior, as described in U.S. Pat. No. 4,059,116, issued to Adams and incorporated herein in its entirety, a sensed depolarization occurring during the extension past the programmed value of SAV is considered to occur outside the SAV interval, and is treated as discussed above. A ventricular pacing pulse delivered at the end of an extended SAV interval is also treated the same as a sensed depolarization outside of the SAV interval.

The ARS pacing mode is preferably automatically activated and deactivated, as opposed to being continuously in effect. If programmed ON, ARS pacing remains in effect unless suspended or programmed OFF. ARS may be suspended, for example, in response to detection or pre-detection of an atrial or ventricular tachyarrhythmia, as discussed in the above cited Peterson et al patent or in response to detection or pre-detection of tachyarrhythmias using alternative detection methodologies. For example, ARS pacing may be suspended in response to a median or mean R-R interval value over a preceding series of a defined number of ventricular events being less than a defined duration. In the context of a device which detects tacharrhytmias based upon defined interval duration ranges, the defined duration may conveniently correspond to the greatest R-R interval duration which is classified as indicative of a ventricular tachycardia or of a fast ventricular tachycardia or of ventricular fibrillation, depending upon which tachyarrhytmias are intended to be treated. ARS pacing may also be suspended in response to a determination that an atrial or ventricular tachycardia is underway or is being treated by an anti-tachycardia therapy or in response to operation of mode switching functions, if the device is so provided. When ARS is suspended the atrial escape interval following non-refractory atrial events is CEI, the same as if ARS is OFF. When ARS pacing resumes from a suspended condition the AAlast will be unknown, with the result that the first ARS interval is set equal to LRI, as discussed above. This prevents atrial events during the suspended condition from affecting ARS operation.

Figure 3:
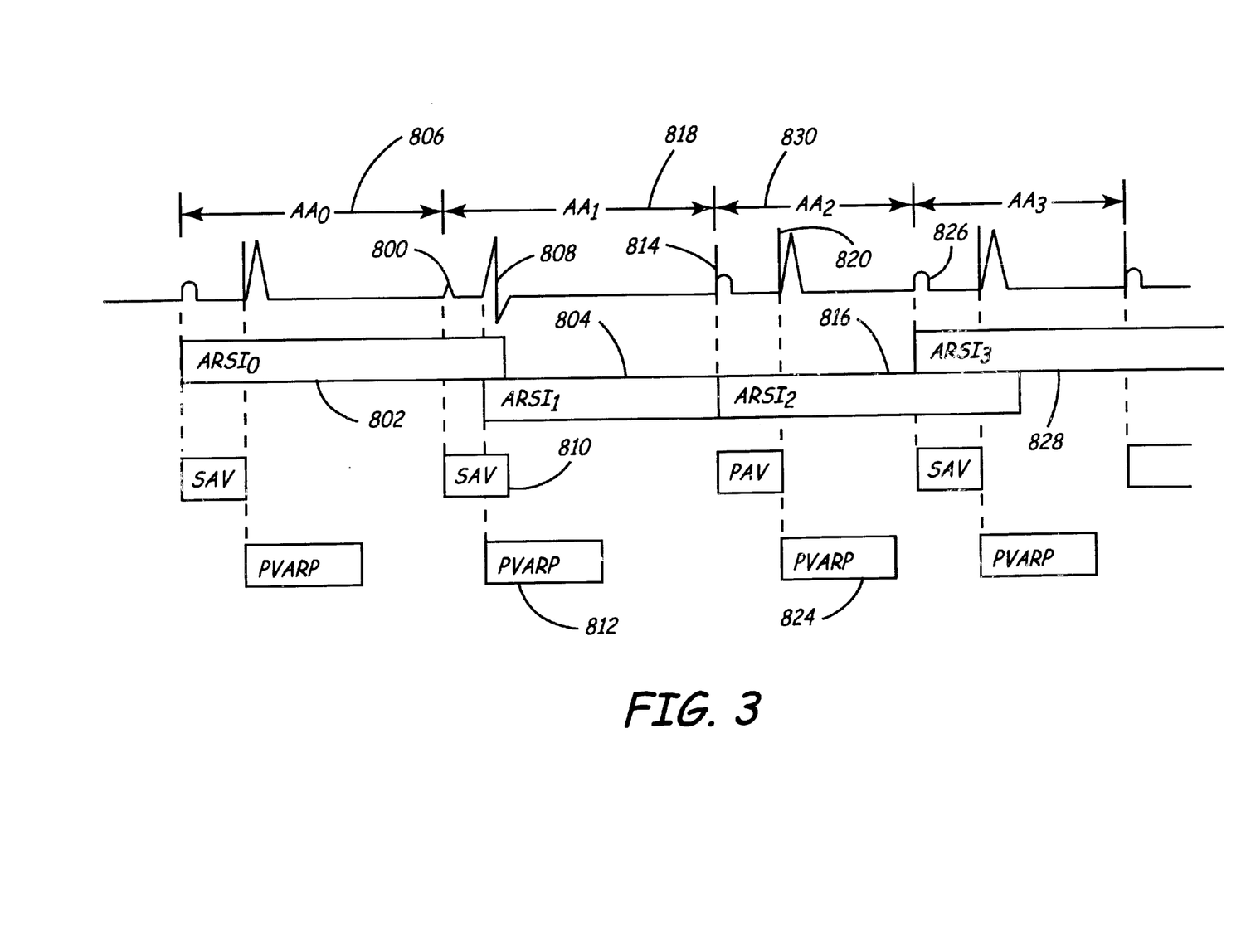
FIGS. 3–5 illustrate the operation of the atrial rate stabilization pacing feature as embodied in the present invention.

In FIG. 3, normal operation of ARS pacing in DDD mode is illustrated. Following a non-refractory sensed atrial depolarization 800, the timing of the atrial escape interval $ARSI_0$ (802) is halted, the $ARSI_1$ cycle length (804) is calculated and is set equal to the preceding A-A interval $AA_0$ (806) plus AARS. On sensing in the ventricle at 808, the scheduled ventricular pacing pulse on expiration of the SAV escape interval 810 is canceled, and PVARP 812 is initiated. On expiration of $ARSI_1$, an atrial pacing pulse is delivered at 814, and $ARSI_2$ (816) is set equal to the preceding A-A interval $AA_1$ (818) plus AARS. A ventricular pacing pulse is delivered at 820, on expiration of the PAV escape interval 822 and PVARP 824 is initiated. In the absence of sensed atrial events, ARSI would be gradually incremented to CEI. However, at 826 a non-refractory atrial depolarization is sensed prior to ARS time-out, causing the value of $ARSI_3$ (828) to be set to the preceding A-A interval $AA_2$ (830) plus AARS. The effect of non-refractory atrial depolarizations in AAI mode is the same.

Figure 4:
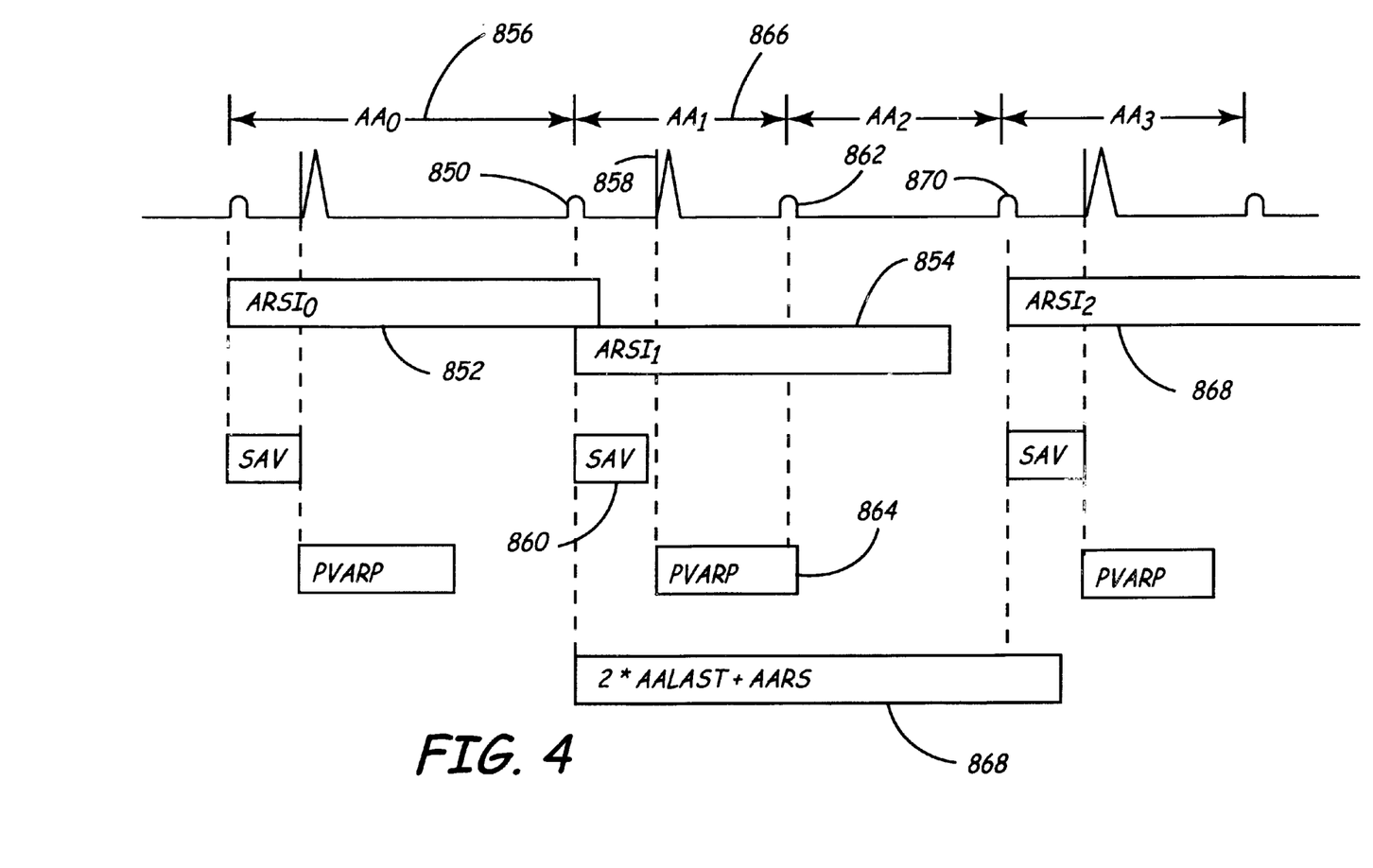

FIG. 4 illustrates the operation of ARS pacing in DDD mode, in response to a refractory sensed atrial depolarization outside the minimum R-P interval. At 850, a non-refractory atrial depolarization is sensed, causing timing of the atrial escape interval $ARSI_0$ (852) underway to be halted and $ARSI_1$ (854)to be set to the preceding A-A interval $AA_0$ (856) plus AARS. At 858, on time-out of the SAV escape interval 860, a ventricular pacing pulse is generated. At 862, an atrial depolarization is sensed within the PVARP 864, but outside the minimum R-P interval. The timing of $ARSI_1$, currently underway is suspended, AAlast is set equal to $AA_1$ (866) and the atrial escape interval is modified so that the next atrial pacing pulse is scheduled to occur on expiration of 2* AAlast+AARS (868) from non-refractory sensed atrial event 850 (equal to AAlast+AARS from refractory sensed depolarization 862). At 870, a non-refractory atrial depolarization is sensed starting timing of $ARSI_2$ (872), which is set equal to $AA_2$ plus AARS. Refractory sensed atrial depolarization 862 is employed for measuring the A-A interval to derive the value of AAlast. for use in this calculation.

Figure 5:
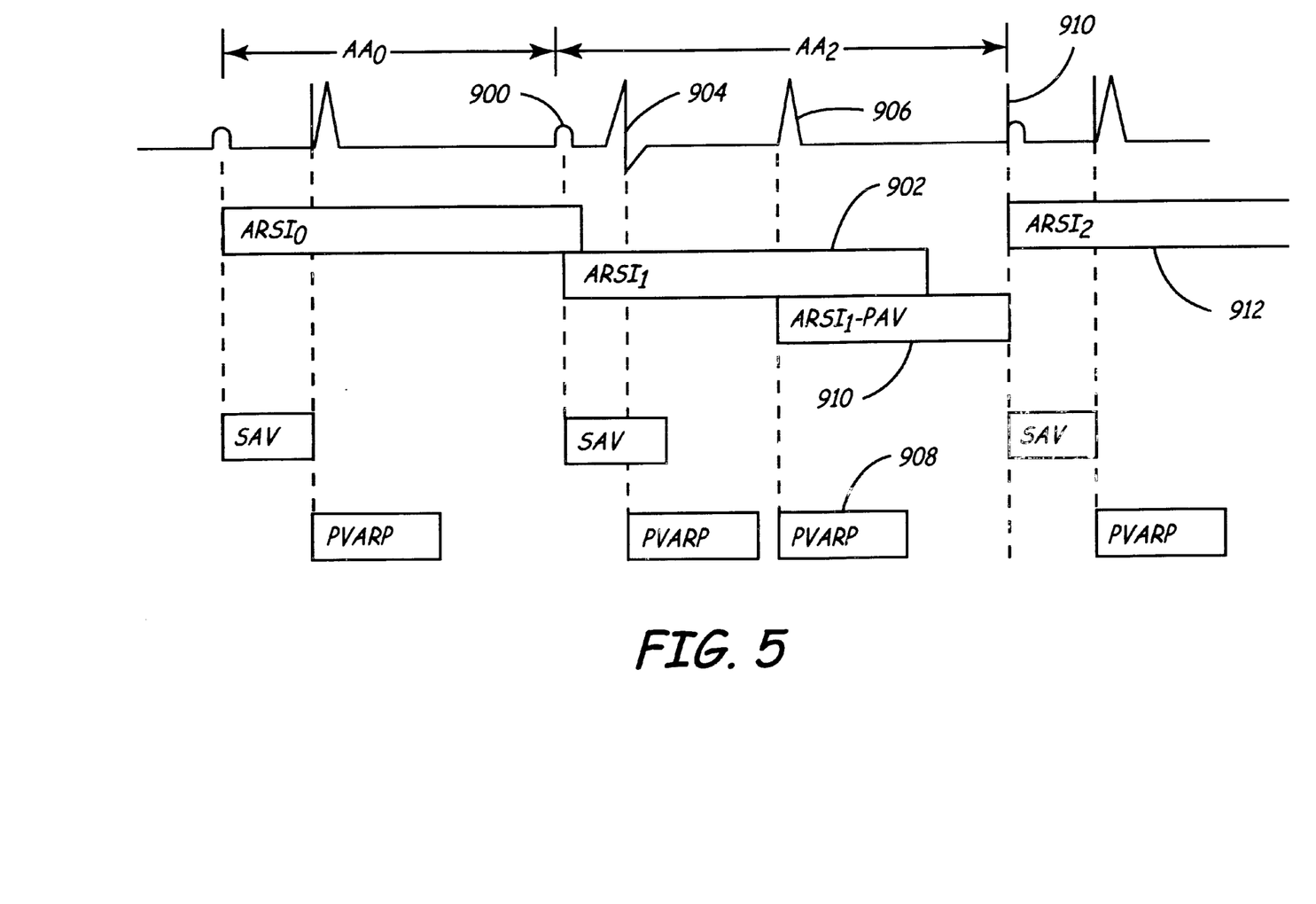

FIG. 5 illustrates the operation of ARS pacing in DDD mode in response to the occurrence of PVC's or other paced or sensed ventricular events which occur outside of a PAV or SAV escape interval. At 900, an atrial event is sensed, initiating timing of $ARSI_1$ (902). At 904 a ventricular depolarization is sensed, followed by a PVC at 906, initiating timing of a new PVARP 908, in this case equal to PVARPpvc. A new atrial escape interval or V-A interval 910 is initiated, equal to $ARSI_1$–PAV . On expiration of the V-A interval, Atrial pacing pulse 910 is generated, and $ARSI_2$ is initiated, set equal to $ARSI_1$+AARS.

ARS pacing in AAI or AAIR modes, unlike typical AAI or AAIR pacing modes employs the device's ventricular sense amplifier to sense ventricular depolarizations, which are used to initiate minimum R-P intervals in the same fashion as in DDD or DDDR modes. Sensed atrial depolarizations outside the minimum R-P intervals cause re-calculation of the ARSI according to the method described above in conjunction with FIG. 3, setting ARSI equal to AAlast+AARS. In AAI and AAIR modes, however, sensed ventricular events do not affect the timing of the atrial escape interval or modify the value of ARSI.

2. APP Pacing

The atrial pacing preference (APP) mode is intended to achieve the maximum amount of atrial pacing while the patient is not in an atrial arrhythmia. Changes to the APP defined pacing interval (APPI) are made after non-refractory sensed atrial events or after the number of consecutive delivered atrial pacing pulses (APP Pace Counter) at least equals the programmed value for APP Delay Beats (APPDB). On a non-refractory atrial sense, the value of APPI is decremented by the APP Decrement (APPID), while following occurrence of the required number of consecutive atrial pacing pulses, APPI is incremented by the APP increment (APPII), and the count of successive delivered atrial pacing pulses (APP Pace Counter) is reset to "0". The values for APPI are bounded by the value of APPImin and by the current escape interval CEI, which may correspond to either the programmed base pacing rate or the sensor indicated pacing rate presently in effect at the time.

In particular, following a non-refractory atrial sense event, APPI is decreased by APPID, within the available bounds of ARSImin and CEI according to the following calculation. APPI=Min (Max (APPI–APPID, APPImin) CEI). As in the case of the calculation of ARSI, if CEI is less than APPImin, CEI defines the next effective escape interval, so that in AAIR and DDDR modes the sensor indicated pacing rate controls. In addition, the value of the APP Pace Counter is reset to "0".

In response to a delivered atrial pacing pulse, the value of the APP Pace Counter is incremented by 1, and is compared to the programmed value for APP Delay Beats. In the event that the APP pace counter is greater than or equal to APP Delay Beats, APPI is increased by APPII, bounded by APPImin and CEI, as discussed above. In this context, the value of APPI is calculated according to the following equation. APPI=Min (Max(APPI+APPII, APPImin) CEI). The APP Pace Counter is also reset to zero.

In the event that the APP Pace Counter is less than APP Delay Beats, the present value of APPI is compared to CEI. If CEI is less than APPI, APPI is set equal to CEI as set forth in the following equation. APPI=Min (Max (APPI, APPImin) CEI). In this manner, APPI remains unchanged unless it is greater than CEI, in which case it is immediately set to CEI. This feature allows variations in CEI, for example, in response to changes in sensor indicated pacing rate, to immediately be applied following atrial pacing pulses, even in the absence of the required number of successive atrial pacing pulses being delivered.

Following any ventricular contraction sensed outside of the SAV or PAV intervals, an atrial escape interval (VA interval) is calculated as set forth in the following equation. VA=Min (APPI, CEI)–PAV. In response to a refractory atrial sensed event, APPI and APP pace counter remain unchanged. Such sensed ventricular events may, for example, be due to premature ventricular contractions or due to ventricular sensing outside of the SAV interval due to delay of a scheduled ventricular pacing pulse until expiration of UTRI.

The APP pacing mode is preferably automatically activated and deactivated, as opposed to being continuously in effect. If programmed ON, APP pacing remains in effect unless suspended or programmed OFF. APP may be suspended, for example, in response to detection or pre-detection of an atrial or ventricular tachyarrhythmia, as discussed in the above cited Peterson et al patent or in response to detection or pre-detection of tachyarrhythmias using alternative detection methodologies. For example, APP pacing may be suspended in response to a median or mean R-R interval value over a preceding series of a defined number of ventricular events being less than a defined duration. In the context of a device which detects tacharrhythmias based upon defined interval duration ranges, the defined duration may conveniently correspond to the greatest R-R interval duration which is classified as indicative of a ventricular tachycardia or of a fast ventricular tachycardia or of ventricular fibrillation, depending upon which tachyarrhythmias are intended to be treated. APP pacing may also be suspended in response to a determination that an atrial or ventricular tachycardia is underway or is being treated by an anti-tachycardia therapy or in response to operation of mode switching functions, if the device is so provided. When APP pacing is suspended, the atrial escape interval following non-refractory atrial events is CEI, the same as if APP is OFF. When APP pacing resumes from a suspended condition the first APP escape interval is set equal to CEI.

Figure 6:
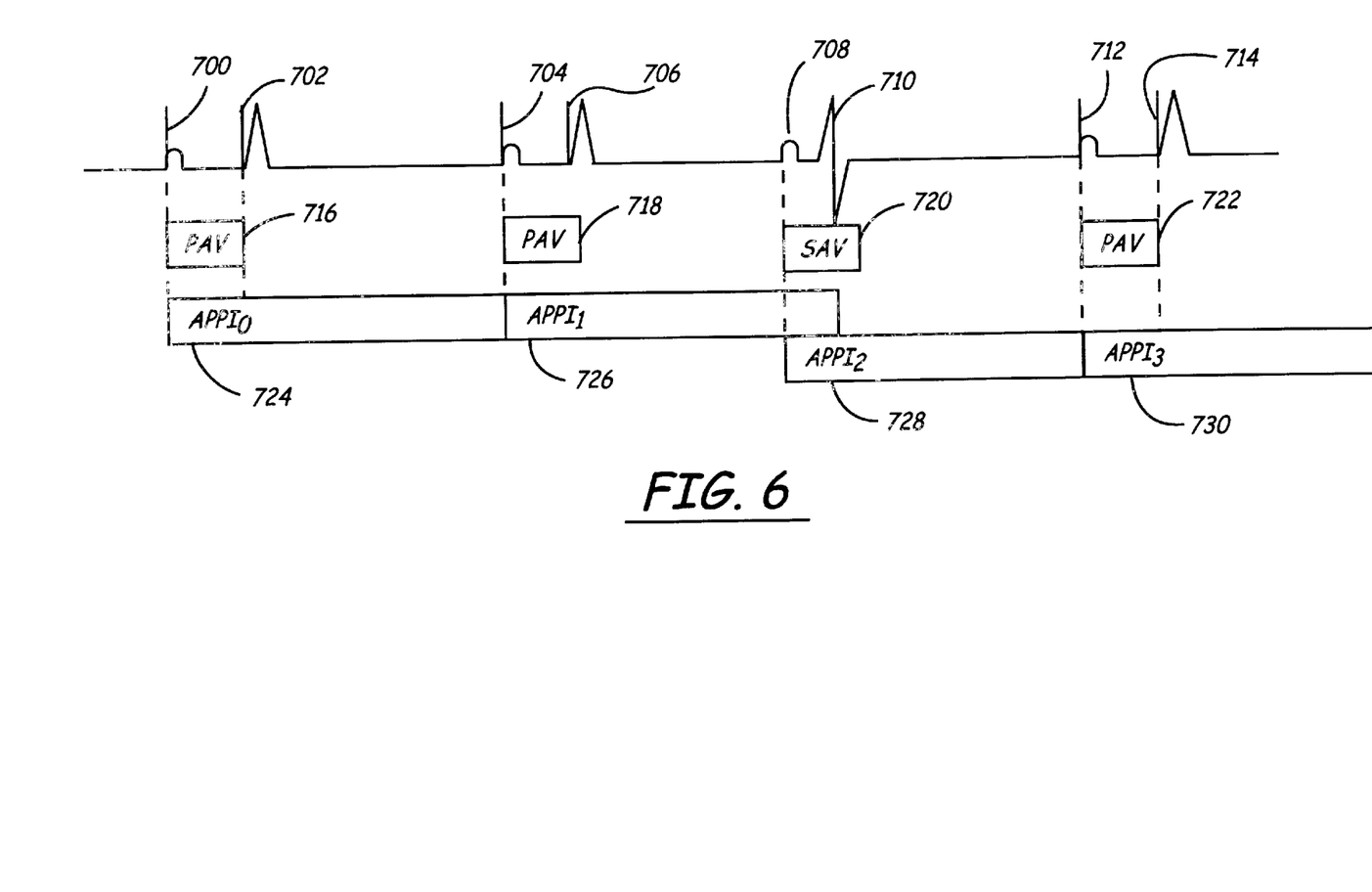
FIGS. 6–8 illustrate the operation of the sinus atrial pacing preference pacing feature as embodied in the present invention.
Figure 7:
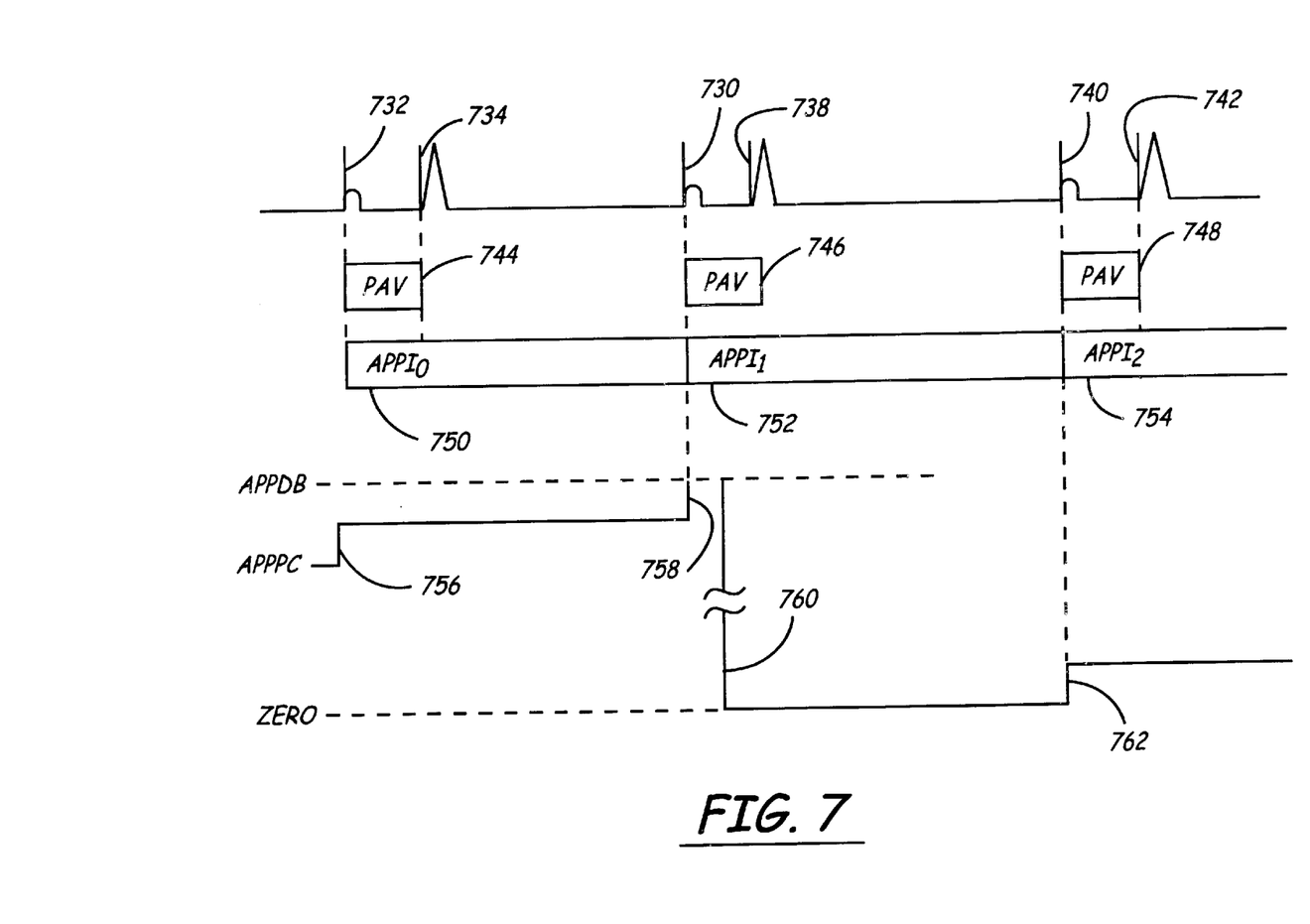
Figure 8:
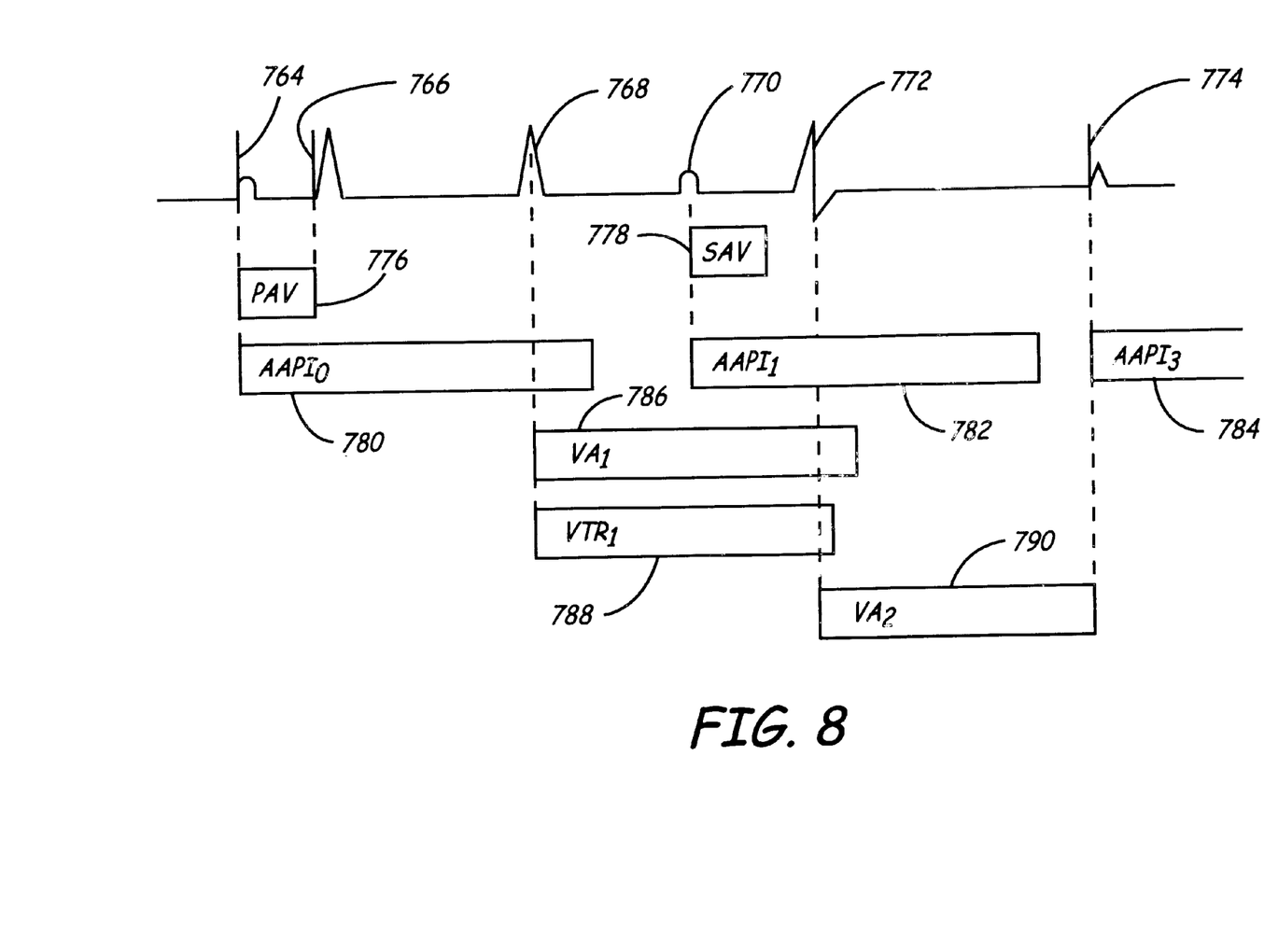

Operation of the device during the APP pacing mode is illustrated in FIGS. 6–8. In FIG. 6, operation of the device following a non-refractory sensed atrial event is illustrated. Atrial and ventricular pacing pulses 700 and 702 separated by PAV interval 716 initiate the simulated electrogram strip. At pacing pulse 700, APP defined escape interval $APPI_0$ is initiated. On expiration of $APPI_0$, an atrial pacing pulse 704 is delivered, followed by ventricular pacing pulse 706 delivered on the expiration of PAV interval 718. Although not illustrated, the APP Pace Counter is incremented at 700. Assuming that the number of successive delivered atrial pacing pulses is less than APP Delay Beats, a new APP defined escape interval APPI, is initiated at 726, and is equal to $APPI_0$. At 708, a non-refractory atrial sense event occurs, followed by a normally conducted ventricular depolarization at 710, prior to expiration of SAV interval 720. On occurrence of non-refractory sensed atrial event 708, a new APP defined escape interval $APPI_2$ is defined at 728. $APPI_2$ is equal to $APPI_1$——APPID. Although not illustrated in FIG. 8, it should be understood that at 708, the value of the APP Pace Counter is reset to "0". On expiration of $APPI_2$, an atrial pacing pulse 712 is delivered followed by a ventricular pacing pulse 714 on expiration of PAV delay 722. Concurrent with delivery of atrial pacing pulse 712, a new APPI escape interval $APPI_3$ is initiated at 720. $APPI_3$ is equal to $APPI_2$.

FIG. 7 illustrates the operation of the device generally in conjunction with the value of the APP Pace Counter (APPPC) equaling APP Delay Beats (APPDB). The simulated electrocardiogram is initiated by delivery of an atrial pacing pulse at 732, followed by a delivery of ventricular pacing pulse at 734, following expiration of PAV interval 744. Concurrent with delivery of atrial pacing pulse 732, an APP escape interval $APPI_0$ is initiated at 750 and the value of the APP Pace Counter is increased at 756. On expiration of $APPI_0$, an atrial pacing pulse is delivered at 730, initiating PAV interval 746, on expiration of which ventricular pacing pulse 736 is delivered. Concurrent with delivery of atrial pacing pulse 730, the APP Pace Counter is incremented at 758, to a value equal to APP Delay Beats, in turn triggering calculation of a new value for the APP defined escape interval, $APPI_1$ at 752. $APPI_1$ is equal to $APPI_0$+APPI. In conjunction with calculation of $APPI_1$ at 752, the APP pacing counter is reset to "0" at 760. On expiration of $APPI_1$, atrial pacing pulse 740 is delivered, initiating PAV interval 748, on expiration of which ventricular pacing pulse 742 is delivered. APP escape interval $APPI_2$ is initiated at 754, following atrial pacing pulse 740, and is equal to $APPI_1$. The value of the atrial pacing pulse counter is incremented at 762, responsive to delivery of atrial pacing pulse 740.

FIG. 8 illustrates the operation of the APP pacing mode in response to ventricular depolarizations sensed outside of SAV or PAV intervals. Delivered atrial pacing pulse 764 initiates the simulated electrocardiogram, followed, on expiration of PAV interval 776 by ventricular pacing pulse 766. APP defined escape interval $APPI_0$ is initiated at 780, following atrial pacing pulse 764. Premature ventricular contraction 768 occurs outside of PAV interval 776, prior to expiration of $APPI_0$. In response thereto, the device calculates an atrial escape interval $VA_1$ equal to $APPI_0$–PAV (776). Initiated concurrent with the ventricular event 768 is a protracting rate interval 788, which, although not illustrated, is of course, initiated in response to other delivered sensed and paced ventricular events. During atrial escape interval $VA_1$ at 786, an intrinsic atrial depolarization 770 occurs, initiating timing of SAV interval 778 and APP defined escape interval $APPI_1$ at 782. Because upper tracking rate interval (UTRI) 788 has not expired on expiration of SAV interval 778, delivery of a ventricular pacing pulse is inhibited until expiration of upper tracking rate interval 788. Spontaneous ventricular depolarization 772 thus occurs outside of SAV interval 778, causing initiation of an atrial escape interval $VA_2$ at 790. $VA_2$ is set equal to $APPI_1$, minus PAV (776). On expiration of escape interval 790, an atrial pacing pulse is delivered at 774 and APP defined escape interval $APPI_3$ is initiated at 784. $APPI_3$ is equal to $APPI_1$.

Figure 9:
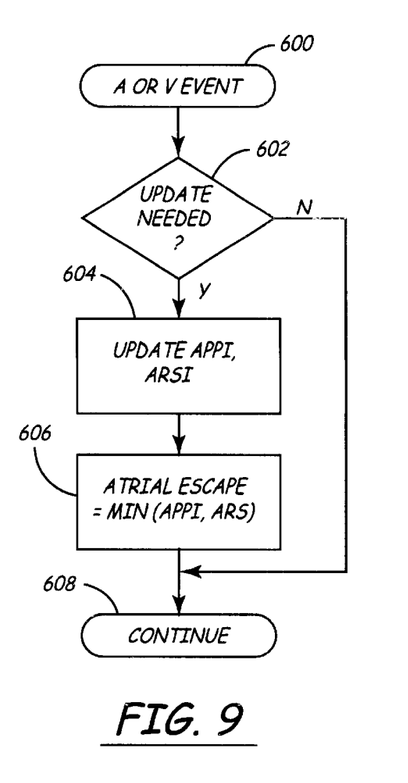
FIGS. 9–11 illustrate the inter-action of the atrial rate stabilization and the atrial pacing preference modes of the present invention to regulate the pacing rate on a beat by beat basis.
Figure 10:
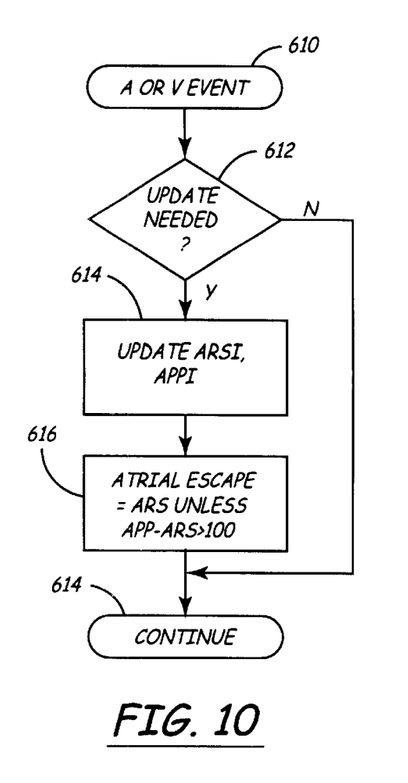
Figure 11:
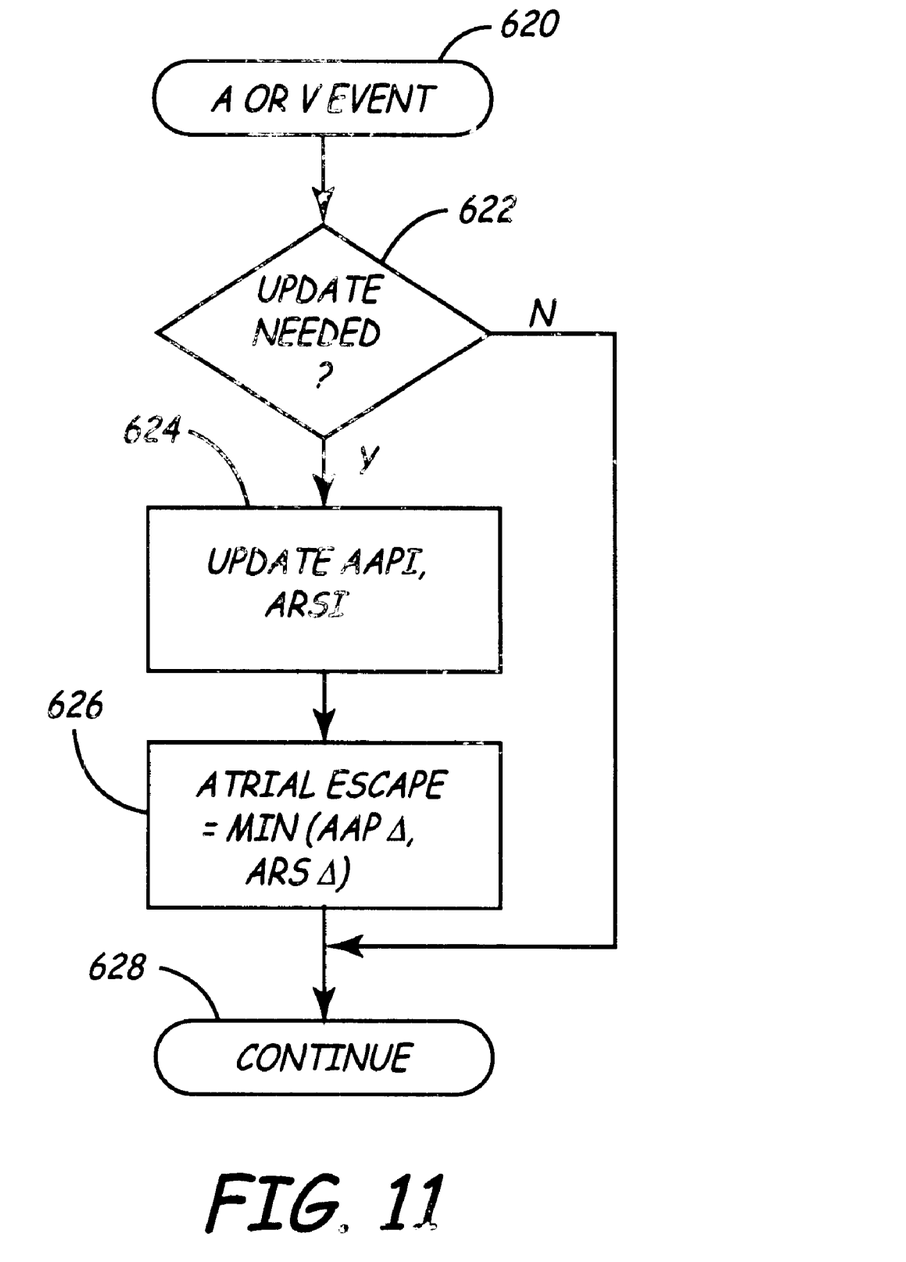

FIGS. 9, 10 and 11 illustrate the operation of a device in which APP pacing and ARSI pacing are simultaneously activated. In this case, values for APPI and ARSI are updated following each event for which an update is appropriate, including sensed atrial events, delivered atrial pacing pulses and ventricular events sensed outside of the SAV or PAV interval. After determining the values of APPI and ARSI, the device selects one of the two values to serve as the next effective atrial escape interval. This value is also employed as the value of APPI in effect for that escape interval, for subsequent calculations of APPI. In the embodiment discussed herein, APP pacing and ARSI pacing are activated and deactivated in response to the same set of events. However, it is within the scope of the invention that they might be activated or deactivated in response to different sets of events, in which case the arrhythmia prevention pacing modality remaining in effect would of course be applied to determine the next successive effective atrial escape interval.

FIG. 9 illustrates the overall operation of the device in which the shortest of the two calculated escape intervals defined according to the APP and ARSI pacing modes is selected to define the escape interval following sensed or paced atrial events and ventricular events occurring outside of SAV or PAV intervals. At 600, an atrial ventricular event occurs, and the device determines whether it is the sort of event which, as discussed above, requires updating of one or both of APP and ARS defined escape intervals at 602. At 604, the device updates the values as needed, and at 606 compares the value of the APP and ARS defined escape intervals, selecting the escape interval which results in the soonest delivery of the next subsequent atrial pacing pulse.

If ARSI is selected as the effective atrial escape interval, the value of APPI is modified to equal ARSI, for use in subsequent calculations of APPI according to the atrial pacing preference mode. At 608 the device continues to perform the other functions associated with updating tachyarrhythmia detection criteria, and/or bradycardia pacing.

FIG. 10 illustrates an embodiment of the invention in which atrial rate stabilization pacing is preferentially applied, unless atrial pacing preference yields an escape interval which is more than 100 milliseconds shorter than atrial rate stabilization pacing. In response to an atrial or ventricular event at 610, the device determines at 612 whether an update of APP or ARS defined escape intervals is necessary. To the extent required, the values are updated at 614 according to the methods described previously, and at 616, the device selects the ARS defined escape interval as the atrial escape interval unless the APP defined Escape interval is more than 100 milliseconds less than the ARS defined escape interval, in which case the APP defined escape interval is selected as the atrial escape interval. If ARSI is selected as the effective atrial escape interval, the value of APPI is modified to equal ARSI, for use in subsequent calculations of APPI according to the atrial pacing preference mode. At 618, the device continues to perform operations associated with tachyarrhythmia detection and bradycardia pacing.

FIG. 11 illustrates the operation of a device in which the device selects the one of APPI and ARSI which provides for the smallest change from the previous atrial escape interval in effect. At 620, following an atrial or ventricular event, the device determines at 622 whether an update of APP or ARS defined escape intervals is required, according to the methods described above. At 624, the values of the APP and/or ARS defined escape intervals are updated according to the methods described above, and at 626, the device determines which of the defined escape intervals represents the minimum change from the preceding atrial escape interval and selects that interval as the effective next atrial escape interval. If ARSI is selected as the effective atrial escape interval, the value of APPI is modified to equal ARSI, for use in subsequent calculations of APPI according to the atrial pacing preference mode. At 628 the device continues operations associated with tachyarrhythmia detection and bradycardia pacing.

While the above FIGS. 9–11 envision the same selection criteria applied to select between APP and ARS defined escape intervals occurring after any events, atrial or ventricular which result in modification of the escape interval defined by either tachyarrhythmia prevention pacing mode, the invention may also be practiced by employing different selection criteria following atrial and ventricular events. For example, in the event that the two tachyarrhythmia prevention pacing modes present yield different results for escape intervals following ventricular events, the lesser of the defined escape intervals might be employed following atrial events, with the greater of the two defined escape intervals or a preselected one of the escape intervals always employed following ventricular events. Likewise, different criteria for selecting between escape intervals following paced and sensed events may also in some cases be beneficial.

While it seems likely that commercial embodiments of a device including the invention will employ a microprocessor in order to perform the calculations and analysis steps required, it is within the realm of possibility that some or all of the functions described above might instead be provided by means of a full custom, integrated circuit, particularly a circuit in which a state counter is employed instead of stored software, in order to control sequential operation of the digital circuitry, along the general lines of the circuits disclosed in U.S. Pat. No. 5,088,488, issued to Markowitz et al. and U.S. Pat. No. 5,052,388, issued to Sivula et al., both of which are incorporated herein by reference in their entireties. Thus, the above description should be considered exemplary, rather than limiting, with regard to the interpretation of the following claims.

In conjunction with the above disclosure, we claim:

1. An implantable pacemaker, comprising:

means for calculating first atrial escape interval according to a first tachyarrhythmia prevention pacing modality;

means for calculating a second atrial escape interval as a function of a second arrhythmia prevention pacing modality; and means for selecting one of said first and second atrial escape intervals as an effective atrial escape interval, following occurrence of a sensed atrial depolarization.

2. An implantable pacemaker, comprising:

a sense amplifier responsive to depolarizations of a chamber of a heart; pacer timing and control circuitry coupled to the sense amplifier and administering multiple tachyarrhythmia prevention pacing modes that are simultaneously active, said pacing modes including an atrial rate stabilization (ARS) pacing mode and an atrial pacing preference (APP) mode;

an escape interval calculator establishing an ARS escape interval (ARSI) and an APP escape interval (APPI); and an escape interval selection circuit that selects one of the ARSI and APPI escape intervals to serve as the effective atrial escape interval during the next cardiac cycle; and a pulse generator coupled to the pacer timing and control circuitry and producing cardiac stimulation pulses in accordance with the pacing mode being administered.

3. The pacemaker of claim 2 wherein the escape interval selection circuit selects the one of ARSI and APPI that provides for the smallest change from the previous escape interval in effect.

4. The pacemaker of claim 2 wherein the escape interval calculator and the escape interval selection circuit comprise a programmed microprocessor performing calculations to establish ARSI and APPI.

5. The pacemaker of claim 4 wherein the microprocessor controls an escape interval timer in the pacer timing and control circuitry.

6. The pacemaker of claim 4 wherein the microprocessor computes ARSI upon the occurrence of each non-refractory atrial event based upon the previous A-A interval, a programmed ARDI increment, the current escape interval (CEI), and a programmed minimum value of ARSI.

7. The pacemaker of claim 4 wherein the microprocessor computes APPI upon the occurrence of each non-refractory atrial event based upon decreasing the APPI then in effect by an APP Decrement value.

8. The pacemaker of claim 2 further comprising:

arrhythmia detection circuitry coupled to the pacer timing and control circuitry;

cardioversion and defibrillation control circuitry coupled to the arrhythmia detection circuitry; and a high voltage output circuit coupled to the cardioversion and defibrillation control circuitry for delivery of cardioversion or defibrillation therapy.

* * * * *